(12) United States Patent
Baltz et al.

(10) Patent No.: US 11,160,278 B2
(45) Date of Patent: Nov. 2, 2021

(54) USE OF ACTIVE SUBSTANCES FOR CONTROLLING VIRUS INFECTION IN PLANTS

(71) Applicant: Bayer CropScience Aktiengesellschaft, Monheim am Rhein (DE)

(72) Inventors: Rachel Baltz, Collonges au Mont d'Or (FR); David Bernier, Lyons (FR); Florence Jay-Brioudes, Zürich (CH); Thomas Knobloch, Alix (FR); Maxime Vitel, Fontaines sur Saône (FR); Olivier Voinnet, Zürich (CH)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 123 days.

(21) Appl. No.: 16/069,462

(22) PCT Filed: Jan. 12, 2017

(86) PCT No.: PCT/EP2017/050585
§ 371 (c)(1),
(2) Date: Jul. 11, 2018

(87) PCT Pub. No.: WO2017/121811
PCT Pub. Date: Jul. 20, 2017

(65) Prior Publication Data
US 2019/0335752 A1    Nov. 7, 2019

(30) Foreign Application Priority Data
Jan. 13, 2016 (EP) .................................. 16290010

(51) Int. Cl.
*A01N 43/42* (2006.01)
*A61K 31/435* (2006.01)

(52) U.S. Cl.
CPC ............ *A01N 43/42* (2013.01); *A61K 31/435* (2013.01)

(58) Field of Classification Search
CPC .............................. A01N 43/42; A61K 31/435
See application file for complete search history.

(56) References Cited

U.S. PATENT DOCUMENTS

| | | | |
|---|---|---|---|
| 8,853,172 B2 | 10/2014 | Masuta et al. | |
| 2003/0139432 A1 | 7/2003 | Kohle et al. | |
| 2004/0082578 A1 | 4/2004 | Heintzelman et al. | |
| 2004/0186149 A1 | 9/2004 | Kohle et al. | |
| 2009/0233916 A1 | 9/2009 | Kohle et al. | |
| 2012/0172580 A1 | 7/2012 | Masuta et al. | |
| 2015/0250169 A1 | 9/2015 | Ihori et al. | |

FOREIGN PATENT DOCUMENTS

| WO | 0182701 A1 | 11/2001 |
|---|---|---|
| WO | 2007104669 A2 | 9/2007 |
| WO | 2009148961 A2 | 12/2009 |
| WO | 2011030816 A1 | 3/2011 |
| WO | 2012016048 A1 | 2/2012 |
| WO | 2014050894 A1 | 4/2014 |

OTHER PUBLICATIONS

Haas et al. (Molecular Plant Pathology (2002) 3(6), 419-429) (Year: 2002).*
Ahmed et al. (Biomed Res Int. 2013; 2013: 367819. Published online Sep. 22, 2013) (Year: 2013).*
Ahmad et al. (Food Research International 77 (2015) 221-235) (Year: 2015).*
English Translation of WO2015049351A1, published Apr. 9, 2015 (Year: 2015).*
PCT International Search Report for PCT/EP2017/050585, dated Mar. 24, 2017.
Zhang, et al., "Chemical Biology in Plants: Finding New Connections between Pathways Using the Small Molecule Sortin 1," Concepts and Case Studies in Chemical Biology, (2014), Wiley-VCH Verlag GmbH & Co. KGaA, Weinheim, Germany, pp. 285-294.
Rosado, et al., "Sortin1-Hypersensitive Mutants Link Vacuolar-Trafficking Defects and Flavonoid Metabolism in *Arabidopsis* Vegetative Tissues," Chemistry & Biology, (2011), vol. 18, No. 2: 187-197.
Treutter, et al., "Significance of Flavonoids in Plant Resistance and Enhancement of Their Biosynthesis," Plant Biology, (2005), vol 7, No. 6: 581-591.
Herms, et al., "A Strobilurin Fungicide Enhances the Resistance of Tobacco against Tobacco Mosaic Virus and Pseudomonas syringae pv tabaci1," Plant Physiology, (2002), vol. 130: 120-127.
Shimura, et al., "Viral induction and suppression of RNA silencing in plants," Biochimica et Biophysica Acta, (2011), vol. 1809: 601-612.
Pumplin, et al., "RNA silencing suppression by plant pathogens: defence, counter-defence and counter-counter-defence," Nature Review Microbiology, (2013), vol. 11: 745-60.
Jan Zouhar, et al., "Sorting inhibitors (Sortins): Chemical compounds to study vacuolar sorting in *Arabidopsis*," PNAS, (2004), vol. 101, No. 25: 9497-9501.
Registry (STN) [online, Apr. 23, 2003, [search date] Oct. 21, 2020, RN: 503837-93-2.
Registry (STN) [online, Aug. 9, 2002, [search date] Oct. 21, 2020, RN: 443289-12-1.
Registry (STN) [online, Aug. 9, 2002, [search date] Oct. 21, 2020, RN: 443123-43-1.
Registry (STN) [online, Aug. 5, 2002, [search date] Oct. 21, 2020, RN: 442568-99-2.
Registry (STN) [online, Jun. 5, 2002, [search date] Oct. 21, 2020, RN: 425627-19-6.

(Continued)

*Primary Examiner* — Kortney L. Klinkel
*Assistant Examiner* — William Y Lee
(74) *Attorney, Agent, or Firm* — McBee Moore & Vanik IP, LLC

(57) ABSTRACT

The use of specific active substances, alone or in combination, for controlling virus infections in plants and a method for using said specific active substances for controlling said virus infections in the field of plant protection and the protection of materials are disclosed.

12 Claims, 1 Drawing Sheet

(56) References Cited

OTHER PUBLICATIONS

Registry (STN) [online, Jun. 4, 2002, [search date] Oct. 21, 2020, RN: 425415-95-8.
Registry (STN) [online, Aug. 24, 2001, [search date] Oct. 21, 2020, RN: 352559-53-6.

* cited by examiner

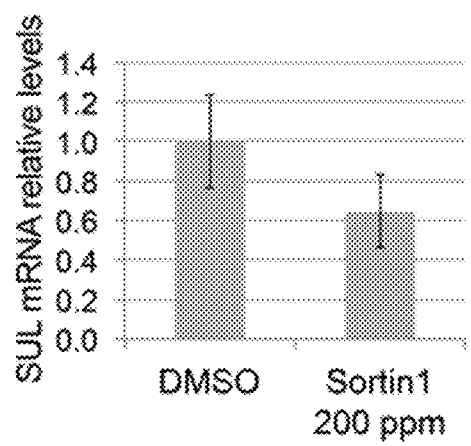

USE OF ACTIVE SUBSTANCES FOR CONTROLLING VIRUS INFECTION IN PLANTS

CROSS-REFERENCE TO RELATED APPLICATIONS

This application is a National Stage entry of International Application No. PCT/EP2017/050585, filed Jan. 12, 2017, which claims priority to European Patent Application No. 16290010.4, filed Jan. 13, 2016.

FIELD

The present invention relates to the use of active substances for stimulating the natural defense mechanism of plants against viruses in order to control virus infections in plants and to methods for controlling virus infections in plants. The present invention also pertains to the use of active substances for activating the RNA-interference-based natural defense mechanism (also designated herein as RNA-silencing-based natural defense mechanism) of plants against viruses.

DESCRIPTION OF RELATED ART

Plant viruses are responsible for major crop damages around the world. Indeed, some virus families, such as the Potyviridae, cause critical yield losses both in developed and emerging countries, conflicting with the ever-increasing food demand. To limit virus infections and spread, disease management is mainly conducted via prevention, as curative treatments are not or poorly efficient.

Several compounds have been identified for trying to control plant viruses.

WO2011/030816 teaches the use of certain ascorbic acid derivatives to control certain plan viruses.

WO2012/016048 provides for the use of azide-modified biomolecules as antiviral agents, including against plant viruses.

WO2014/050894 teaches the use of other ascorbic acid related compounds to control plant viruses.

Plants have evolved to continuously cope with threats using their available resources and balancing them between growth or defense against biotic and abiotic threats. RNA silencing plays a major part in this balance by dynamically linking developmental programs and environmental stress responses to gene expression changes through transcriptional gene silencing (TGS) and post-transcriptional gene silencing (PTGS). Disease resistance in plants relies on preformed barriers, toxic secondary metabolites and inducible defense mechanisms. Upon pathogen recognition, plants often initiate hypersensitive response, leading to cell death at the infection site and preventing the pathogen from spreading. In addition, pathogen detection triggers various inducible systemic defenses, in parts of the plant distant from the primary infection site. This process, known as Systemic Acquired Resistance (SAR), is effective in many plant species. The resistance achieved is long-lasting and effective against subsequent infections by a broad range of pathogens e.g. fungi, bacteria and viruses.

The Strobilurin class of fungicides comprises a variety of synthetic plant-protecting compounds with broad-spectrum. In 2002, the strobilurin Pyraclostrobin has been demonstrated to enhance the resistance of tobacco against infection by either tobacco mosaic virus (TMV) or the wildfire pathogen *Pseudomonas syringae* pv *tabaci* (Herms et al., Plant Physiology 2002, 130: 120-127). Pyraclostrobin was also able to enhance TMV resistance in NahG transgenic tobacco plants unable to accumulate significant amounts of the endogenous salicylic acid. Pyraclostrobin enhances TMV resistance in tobacco either by acting downstream of Salicylic Acid (SA) in the SA signaling mechanism or by functioning independently of SA. The latter assumption is the more likely because, in infiltrated leaves, Pyraclostrobin did not cause the accumulation of SA-inducible pathogenesis-related (PR)-1 proteins that often are used as conventional molecular markers for SA-induced disease resistance. Application of strobilurins is described either alone (WO 01/82701) or in mixture with metiram (WO 2007/104669).

Among the plant defense responses to phytoviruses, the antiviral RNA silencing pathway is the broadest defense system affecting both the local and the systemic accumulation of a wide range of viruses. RNA silencing is a mechanism that directly defends plant host cells against exogenous nucleic acids, including viruses and transposable elements. This defense is triggered by double-stranded RNA (dsRNA), derived from amplification of invasive nucleic acids, which is processed by the host into small interfering RNAs (siRNAs) that are 20-24 nucleotides (nt) in size. These siRNAs are then used to guide the silencing of the viral or transposable element RNA or DNA through PTGS or TGS, respectively.

RNA silencing is then a potent antiviral mechanism whereby small interfering siRNAs processed by the enzyme Dicer from viral double-stranded RNA replication intermediates are loaded into ARGONAUTE effector proteins and turned back onto the invader's RNA genome to induce its degradation. This innate immune response is remarkably versatile because, being solely programmed by structural and nucleotide-sequence genomic features, it can respond to virtually any plant virus (Shimura et al., 2011, *Biochimica et Biophysica Acta* 1809: 601-612).

Attesting the importance of RNA silencing in plant defense, plants impaired in siRNA production or activity are hyper-susceptible to phytoviruses, and conversely many viruses have evolved suppressors of RNAi in order to maintain virulence (Voinnet O. et al, Nature Review Microbiology 2013 November; 11(11):745-60).

In conclusion, although certain compounds have been identified in the past as potential inducers of certain plant defense mechanisms against viruses, there remains a need to provide active substances suitable for stimulating the natural defense mechanism of plants against viruses, in particular for stimulating the broad non-specific RNA-silencing-based defense mechanism of plants against viruses in order to control viral diseases in plants.

DEFINITIONS

The term "halogen" as used herein refers to a fluorine, chlorine, iodine or bromine atom.

The term "phenylthio" as used herein refers to the radical —S-phenyl.

The term "carboxy" as used herein refers to the radical —COOH.

The term "nitro" as used herein refers to the radical —NO$_2$.

The term "active substance" as used herein designates a compound of formula (I) as described herein or any mixtures thereof.

FIG. 1 illustrates the qPCR analysis of the SUL mRNA relative levels in SUC-SUL plants seven days after treatment with DMSO only or Sortin1, normalized to EXP10. Error bars represent standard deviation from three independent experiments.

SUMMARY

It has now been found that compounds of formula (I) as disclosed herein are suitable for stimulating the natural defense mechanism of plants against viruses, in particular for stimulating the RNA-silencing-based defense mechanism of plants against viruses. Therefore, the compounds of formula (I) as disclosed herein may be useful for controlling viral diseases in plants. The term "control" or "controlling" as used herein designates a preventive or curative control.

Accordingly, the present invention relates to a method for controlling viral diseases in plants, more specifically to a method for stimulating the natural defense mechanism of plants against viruses, in particular for stimulating the RNA-silencing-based defense mechanism of plants against viruses. The method comprises applying to the plants one or more compounds of formula (I):

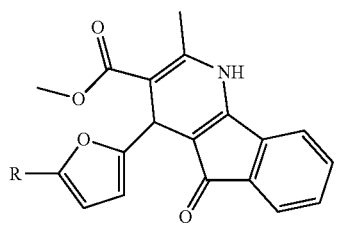

(I)

wherein R is selected from the group consisting of hydrogen, phenylthio and substituted phenyl, wherein said phenyl is substituted with one or more substituents independently selected from the group consisting of halogen, preferably chlorine, fluorine and bromine, carboxy and nitro.

In some embodiments, the active substance is a compound of formula (I) wherein R is a hydrogen, a phenylthio or a phenyl substituted with one or two substituents independently selected from the group consisting of halogen, preferably chlorine, fluorine and bromine, carboxy and nitro.

In some preferred embodiments, the active substance is a compound of formula (I) wherein R is selected from the group consisting of hydrogen, phenylthio, 2-carboxyphenyl, 4-carboxyphenyl, 3-chlorophenyl, 3,4-dichlorophenyl, 2,5-dichlorophenyl, 3-carboxy-4-chlorophenyl, 2-nitrophenyl and 2-bromo-4-nitrophenyl.

BRIEF DESCRIPTION OF THE DRAWINGS

FIG. 1 illustrates the qPCR analysis of the SUL mRNA relative levels in SUC-SUL plants seven days after treatment with DMSO only or Sortin1, normalized to EXP10. Error bars represent standard deviation from three independent experiments.

DETAILED DESCRIPTION OF A PREFERRED EMBODIMENT

In some more preferred embodiments, the active substance is a compound of formula (I) wherein R is 4-carboxyphenyl. Said compound is known as Sortin 1.

Sortin1 belongs to sorting inhibitors that stimulate secretion in yeast. It is known to redirect the vacuolar destination of plant carboxypeptidase Y (CPY) and other proteins in Arabidopsis suspension cells and cause these proteins to be secreted. Similar treatment of whole Arabidopsis seedlings also resulted in the same effect, indicating that the drug has a similar mode of action in cells and intact plants (Zouhar et al., PNAS 2004, 101, 25:9497-9501). In Arabidopsis, Sortin1 has reversible effects on CPY vacuole targeting, vacuole biogenesis, and root development. Sortin1 is highly specific in affecting targeting of a tonoplast marker as well as the biogenesis of vacuoles but not the Endoplasmic Reticulum, Golgi, or endosomes (Hicks et al., Current Opinion in Plant Biology 2010, 13:706-713).

Some compounds of formula (I) are commercially available. Some others may be suitably prepared by methods disclosed in WO2002085894, US20040082578, "Multicomponent one-pot solvent-free synthesis of functionalized unsymmetrical dihydro-1H-indeno[1,2-b]pyridines": Samai, Chandra Nandi, Kumar, Singh, Tetrahedron Lett. 2009, 50(50), 7096-7098.

An effective amount of active substance is typically applied to the plants. The effective amount of active substance which is applied to the plants will depend on various factors, such as the nature of the active substance, the formulation, the plants being targeted (plants nature and plants part), the application method, the purpose of the treatment (prophylactic or therapeutic) and the virus being targeted. The amount applied to the plants may suitably range from 0.01 to 5 kg/ha, or from 0.1 to 3 kg/ha, or from 0.5 to 2 kg/ha.

As indicated above, the active substance is applied to the plants. The term "plants" as used herein include plants and parts thereof, such as the aerial and/or subterraneous parts of the plants as well as the harvested material. Subterraneous plants parts include root, rhizomes, tubers, suckers, slips, seeds and seed. The aerial plant parts include stem, bark, shoot, leaf, flower, fruits, fruiting bodies, stalk, needles and branches. Thus, the active substance may be efficiently applied to the root, rhizomes, tubers, suckers, slips, seeds, seed, stem, bark, shoot, leaf, flower, fruits, fruiting bodies, stalk, needles, branches, harvested material of the plants. In alternative embodiments, the method for controlling viral diseases in plants comprises applying the disclosed active substance to the plants' habitat and/or store.

The active substance can be efficiently applied to a large variety of plants. It may be applied to plants of the varieties which are commercially available or in use. However, plant varieties are also understood as meaning plants with novel traits which have been bred either by traditional breeding, by mutagenesis or with the aid of recombinant DNA techniques and/or to plants which can be obtained by traditional breeding and optimization methods or else by biotechnological and genetic engineering methods or by combinations of these methods; this includes the transgenic plants and the plants which are capable or not of being protected by Plant Breeders' Rights.

The active substance may also be efficiently applied to genetically modified organisms (GMOs). Genetically modified plants are plants in which a heterologous gene has been stably integrated into the genome. The expression "heterologous gene" essentially means a gene which has been provided or assembled outside the plants and, when introduced into the nuclear, chloroplastic or mitochondrial genome, imparts novel or improved agronomic or other properties to the transformed plant by expressing a protein or polypeptide of interest or by down regulating or silencing another gene which is present in the plant, or other genes which are present in the plant (using, for example, antisense technology, cosuppression technology or RNAi technology [RNA interference]). A heterologous gene that is located in the genome is also called a transgene. A transgene that is defined by its particular location in the plant genome is referred to as a transformation event, or transgenic event.

All plants which have genetic material which imparts, to these plants, especially advantageous, useful traits (whether obtained by breeding and/or by biotechnology) may be treated by the disclosed method.

Plants and plant varieties which can likewise be treated in accordance with the invention are those plants which are resistant to one or more abiotic stress factors. Abiotic stress conditions can include, for example, drought, chill and heat conditions, osmotic stress, water-logging, elevated soil salt content, elevated exposure to minerals, ozone conditions, high-light conditions, limited availability of nitrogen nutrients, limited availability of phosphorus nutrients or the avoidance of shade.

Plants and plant varieties which can likewise be treated in accordance with the invention are those plants which are characterized by enhanced yield characteristics. Enhanced yield in these palm plants can be the result of, for example, improved plant physiology, improved plant growth and improved plant development, such as water utilization efficiency, water retention efficiency, improved nitrogen utilization, improved carbon assimilation, improved photosynthesis, increased germination efficiency and modified maturation. The yield can furthermore be influenced by improved plant architecture (under stress conditions and under nonstress conditions), among which early flowering, flowering control for the production of hybrid seed, seedling vigour, plant size, internode number and distance, root growth, seed size, fruit size, pod size, pod or ear number, number of seeds per pod or ear, seed mass, enhanced seed filling, reduced seed dispersal, reduced pod dehiscence, and lodging resistance. Further yield traits include seed composition, such as carbohydrate content, protein content, oil content and oil composition, nutritional value, reduction in antinutritional compounds, improved processability and improved storability.

Plants which can likewise be treated in accordance with the invention are hybrid plants that already express the characteristics of heterosis, or hybrid vigour, which generally results in higher yield, higher vigour, better health and better resistance to biotic and abiotic stress factors. Such plants are typically generated by crossing an inbred male-sterile parent line (the female parent) with another inbred male-fertile parent line (the male parent). The hybrid seed is typically harvested from the male-sterile plants and sold to growers. Male-sterile plants can sometimes (for example in maize) be generated by detasseling (i.e. the mechanical removal of the male reproductive organs or the male flowers); however, more typically, male sterility is the result of genetic determinants in the plant genome. In this case, in particular when seed is the desired product which is to be harvested from the hybrid plants, it is typically useful to ensure that male fertility in hybrid plants which contain the genetic determinants responsible for male sterility is fully restored. This can be achieved by ensuring that the male parents have appropriate fertility restorer genes which are capable of restoring male fertility in hybrid plants which contain the genetic determinants responsible for male sterility. Genetic determinants for male sterility can be located in the cytoplasm. Examples of cytoplasmic male sterility (CMS) have been described for example for *Brassica* species (WO 1992/005251, WO 1995/009910, WO 1998/27806, WO 2005/002324, WO 2006/021972 and U.S. Pat. No. 6,229,072). However, genetic determinants for male sterility may also be located in the nuclear genome. Male-sterile plants can also be obtained by plant biotechnology methods, such as genetic engineering. A particularly advantageous means for generating male-sterile plants is described in WO 89/10396, in which, for example, a ribonuclease such as a barnase is selectively expressed in the tapetum cells in the stamens. The fertility can then be restored by expression in the tapetum cells of a ribonuclease inhibitor such as barstar (for example WO 1991/002069).

The active substance is particularly suitable for controlling viral diseases in the following plants: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp. (for example banana trees and plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumber), *Alliaceae* sp. (for example leek, onion), *Papilionaceae* sp. (for example peas); major crop plants, such as *Gramineae* sp. (for example maize, turf, cereals such as wheat, rye, rice, barley, oats, millet and triticale), *Asteraceae* sp. (for example sunflower), *Brassicaceae* sp. (for example white cabbage, red cabbage, broccoli, cauliflower, Brussels sprouts, pak choi, kohlrabi, radishes, and oilseed rape, mustard, horseradish and cress), *Fabacae* sp. (for example bean, peanuts), *Papilionaceae* sp. (for example soya bean), *Solanaceae* sp. (for example potatoes), *Chenopodiaceae* sp. (for example sugar beet, fodder beet, swiss chard, beetroot); useful plants and ornamental plants for gardens and wooded areas; and genetically modified varieties of each of these plants.

More specifically, the active substance is suitable for controlling viral diseases in vegetable plants.

The active substance is particularly suitable for controlling viruses of the following families or genus: *Caulimoviridae, Geminiviridae, Bromoviridae, Closteroviridae, Comoviridae Potyviridae, Sequiviridae, Tombusviridae, Rhabdoviridae, Bunyaviridae, Partitiviridae, Rheoviridae, Capillovirus, Carlavirus, Enamovirus, Furovirus, Hordeivirus, Idaeovirus, Luteovirus, Marafivirus, Potexvirus, Sobemovirus, Tenuivirus, Tobamovirus, Tobravirus, Trichovirus, Tymovirus* and *Umbravirus*.

Preferably, the active substance is used for controlling viruses of the following species: Turnip mosaic virus, bean pod mottle virus, cauliflower mosaic virus, tobacco mosaic virus, tomato bushy stunt virus, rice ragged stunt virus, cucumber mosaic virus, barley yellow dwarf virus, beet yellows virus, lettuce yellows virus, maize mosaic virus, peanut stunt virus and potato virus Y.

The active substance can be applied to the plants in any suitable forms. For example, the active substance may be applied in the form of a suspension, e.g. water- or oil-based suspension, emulsion, solution, powder such as wettable powder, foam, paste, granules, microparticles, aerosols or microencapsulations. Suitable formulations can be prepared in conventional manners. The formulations comprising the active substance may be ready-for-use compositions, i.e. compositions that can be directly applied to the plants by a suitable device, or they may be in the form of commercial concentrates which have to be diluted prior to use.

The formulations may comprise the active substance alone or in combination with other active substances such as insecticides, attractants, sterilants, bactericides, acaricides, nematicides, further fungicides, growth-regulating substances, herbicides, safeners and/or fertilizers.

The active substance or formulations comprising thereof may be applied to the plants in any customary manners, e.g. watering, spraying, dusting, atomizing. The active substance may be directly or indirectly applied to the plants, the environment, the habitat and/or the store. For example, the active substance can be injected into or below the bark, poured or sprayed around the plant onto the ground (soil, sandy soil, gravelly soil, rocky soil, loamy soil or mixed soil). A further type of application is the spraying onto the plant and its plant parts. In dry form, the active substance composition can be admixed to the ground material (soil, sandy soil, gravelly soil, rocky soil, loamy soil or mixed soil) and/or to the seeds. The active substance can be applied to the irrigation system, either in dry or else in liquid form. The active substance is preferably applied to the plants by spraying.

The present invention also relates to the use of compounds of formula (I) as disclosed herein for controlling viral diseases in plants, more specifically for stimulating the natural defense mechanism of plants against viruses, in particular for stimulating the RNA-silencing-based defense mechanism of plants against viruses. The plants and/or viruses are as disclosed above.

The compounds of formula (I) stimulate the RNA-silencing-based defense mechanism of the plants through an increase in small RNA production. Advantageously, the ability of the compounds of formula (I) to increase small RNA production can also be used in genetically modified plants transformed with an RNAi construct designed to improve agronomic traits and/or to provide resistance against pathogens (e.g. bacteria, fungi), resistance against insect/pest and/or stress tolerance. Therefore, the present invention also relates to the use of one or more compounds of formula (I) to improve agronomic traits and/or to provide resistance against pathogens, resistance against insect/pest and/or stress tolerance in genetically modified plants transformed with an RNAi construct through enhancement of small RNA production.

As previously mentioned, plants are known to use the RNA silencing pathway to fend off invading viruses. In mammals, until the recent findings of Y. Li et al. and P. V. Maillard et al. (Y. Li et al., *Science,* 342: 231-234, 2013; P. V. Maillard et al., *Science,* 342: 235-238, 2013), scientists could only evidence the gene-regulatory role of RNAi. Now, Y. Li et al. and P. V. Maillard et al. have evidenced that RNAi also acts as an antiviral response in mammals. Hence, the compounds of formula (I) can be used for stimulating the natural defense mechanism of mammals against viruses, in particular for stimulating the RNA-silencing-based defense mechanism of mammals against viruses.

Therefore the present invention also relates to compounds of formula (I) as disclosed herein for use as a medicament, in particular for use in the treatment or prevention of a viral infection.

The compound of formula (I) as disclosed herein may be used in a method for treating or preventing a viral infection in mammals which comprises administrating to a mammal in need thereof an effective amount of a compound of formula (I) as disclosed herein. The term "mammals" as used herein includes humans.

The present invention is explained in greater detail with the aid of the examples which follow.

EXAMPLES

Example 1: Identification of Modulators of Plant's Silencing Machinery—Use of SUC-SUL Reporter Plants The plants' RNA silencing pathway can be easily monitored with the artificially-created reporter plants called the "SUC-SUL *Arabidopsis* reporter plants" (Dunoyer et al., Nat. Genet. 37, 1356-1360, 2005).

The SUC-SUL *Arabidopsis* reporter plants are transgenic plants expressing an inverted-repeat (IR) double-stranded RNA designed to target the SULPHUR (SUL) transcript in the vasculature under the control of the SUC2 promoter (Truernit et al., Planta 196(3), 564-570, 1995). Once expressed, the dsRNA is processed into small interfering RNAs directing non-cell autonomous post-transcriptional gene silencing of the SULPHUR transcript, in turn causing vein-centered chlorosis. Since the observed chlorosis results from the silencing of the SULPHUR transcript, an expansion of the chlorosis, observable directly on the plants, is correlated with an intensification of the RNA silencing pathway at the molecular level.

Five days post-germination *A. thaliana* seedlings were sprayed with different solutions containing 300 ppm of an active molecule according to the invention, with dimethylsulfoxide (DMSO) 5% and a standard emulsifiable concentrate (EC) premix formulation (6 seedlings/test). Four repetitions were performed for each molecule. Control plants were treated with DMSO only (mock treated plants). The effects of the treatments on the SUC-SUL reporter plants were assessed 14 days after treatment under trans-illumination and digitally recorded with a stereo-microscope by measuring the surface and intensity of the chlorotic zone (percentage of chlorosis). Two independent experiments were carried out in order to estimate the average percentage of chlorosis for each molecule.

Results are shown in table 1 below. Treatment with 300 ppm of Sortin1 and analogues thereof led to a significant increase in the percentage of chlorosis confirming the activity of the active substance as putative robust enhancers of RNA silencing.

In order to discard molecules acting straightly on the promoter and not on the RNA silencing machinery, the active substances identified for their ability to increase the surface and intensity of the chlorotic zone were then tested, in a second step, on some AtSUC2-GFP reporter plants, which are specifically reporting the activity of the SUC2 promoter (Wright et al., Plant Physiol. 131, 1555-1565, 2003).

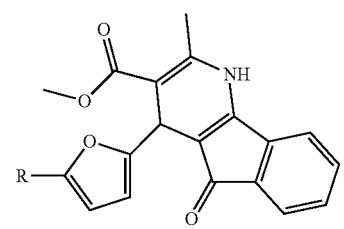

TABLE 1

Evaluation of Sortin1 (compound ID No. 1) and analogs thereof on SUC-SUL reporter plants. The level of chlorosis of mock treated plant reached 10%.

| ID | R | Average % chlorosis |
|---|---|---|
| 1 | 4-carboxyphenyl | 34.0 |
| 2 | 2-carboxyphenyl | 33.2 |
| 3 | 3,4-dichlorophenyl | 31.0 |
| 4 | 3-carboxy-4-chlorophenyl | 29.9 |
| 5 | 2-nitrophenyl | 26.6 |
| 6 | SPh | 23.1 |
| 7 | 3-chlorophenyl | 21.5 |
| 8 | 2,5-dichlorophenyl | 21.4 |
| 9 | H | 20.6 |
| 10 | 2-bromo-4-nitrophenyl | 19.1 |

Example 2: Confirmation of the Molecular Effect of the Silencing Modulators

The enhancing effect of Sortin1 on the RNAi machinery has been validated at the phenotypic and molecular levels. Four-week-old SUC-SUL *Arabidopsis* plants at rosette stage were sprayed with Sortin1 at 200 ppm. Seven days after treatment, it was shown that Sortin 1 induced a clear expansion of the RNAi-dependent vein-centered chlorotic phenotype, which was not observed with DMSO only (mock control).

The plant aerial tissues were collected and analyzed molecularly using state-of-the-art methodologies. The visual expansion of the chlorosis correlated with reductions in SUL transcript levels, as analyzed by real-time qRT-PCR (FIG. 1), as well as reductions in SUL protein levels quantifiable on Western blot analyses. Furthermore, these effects were associated with an over-accumulation of both 21-nt and 24-nt long siRNAs derived from the transgenic SUL. Altogether, these data support that Sortin1 induces the plant's RNAi pathway.

The invention claimed is:

1. A method for controlling viral disease in plants, which comprises applying to the plants at least one compound of formula (I):

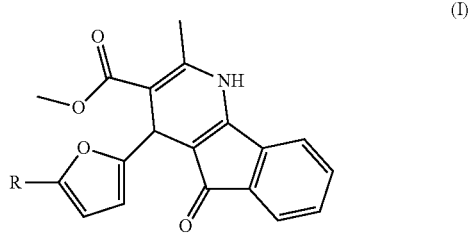

(I)

wherein R is selected from the group consisting of hydrogen, phenylthio and substituted phenyl, wherein said phenyl is substituted with one or more substituents independently selected from the group consisting of halogen, carboxy and nitro.

2. The method according to claim 1, wherein R is selected from the group consisting of hydrogen, phenylthio, 2-carboxyphenyl, 4-carboxyphenyl, 3-chlorophenyl, 3,4-dichlorophenyl, 2,5-dichlorophenyl, 3-carboxy-4-chlorophenyl, 2-nitrophenyl and 2-bromo-4-nitrophenyl.

3. The method according to claim 1, wherein R is 4-carboxyphenyl.

4. The method according to claim 1, wherein the control is based on a stimulation of the natural defense mechanism of plants against viruses.

5. The method according to claim 4, wherein the natural defense mechanism of plants against viruses is a RNA-silencing based plant defense mechanism.

6. The method according to claim 1, wherein said method is a preventive method.

7. The method according to claim 1, wherein said plants are selected from the group consisting of cotton, flax, grapevine, fruit, vegetables, crop plants, ornamental plants for gardens and wooded area and genetically modified varieties of each of these plants.

8. The method according to claim 1, wherein said plants are selected from the group consisting of *Ribesioidae* sp., *Juglandaceae* sp., *Betulaceae* sp., *Anacardiaceae* sp., *Fagaceae* sp., *Moraceae* sp., *Oleaceae* sp., *Actinidaceae* sp., *Lauraceae* sp., *Musaceae* sp., *Rubiaceae* sp., *Theaceae* sp., *Sterculiceae* sp., *Rutaceae* sp.; *Solanaceae* sp., *Liliaceae* sp., *Asteraceae* sp., *Umbeffiferae* sp., *Cruciferae* sp., *Chenopodiaceae* sp., *Cucurbitaceae* sp., *Affiaceae* sp., *Papilionaceae* sp., *Asteraceae* sp., *Brassicaceae* sp., *Fabacae* sp., *Papilionaceae* sp., *Solanaceae* sp. and *Chenopodiaceae* sp..

9. The method according to claim 1, wherein said viruses are selected from the group consisting of the following families or genus:
*Caulimoviridae, Geminiviridae, Bromoviridae, Closteroviridae, Comoviridae Potyviridae, Sequiviridae, Tombusviridae, Rhabdoviridae, Bunyaviridae, Partitiviridae, Rheoviridae, Capillovirus, Carla virus, Enamovirus, Furovirus, Hordeivirus, ldaeovirus, Luteovirus, Marafivirus, Potexvirus, Sobemovirus, Tenuivirus, Tobamovirus, Tobravirus, Trichovirus, Tymovirus* and *Umbra virus*.

10. The method according to claim 1, wherein said viruses are selected from the group consisting of Turnip mosaic virus, bean pod mottle virus, cauliflower mosaic virus, tobacco mosaic virus, tomato bushy stunt virus, rice ragged stunt virus, cucumber mosaic virus, barley yellow dwarf virus, beet yellows virus, lettuce yellows virus, maize mosaic virus, peanut stunt virus and potato virus Y.

11. The method according to claim 1, wherein the compound of formula (I) is applied by spraying to the plants.

12. The method according to claim 1, wherein the compound of formula (I) is applied to the plants in an amount ranging from 0.01 to 5 kg/ha.

* * * * *